United States Patent
Hanai et al.

(12)

(10) Patent No.: US 8,008,084 B1
(45) Date of Patent: Aug. 30, 2011

(54) METHOD FOR DETERMINING WHETHER OR NOT A MAMMAL IS AFFECTED WITH A LUNG CANCER

(75) Inventors: Yosuke Hanai, Osaka (JP); Yuki Sugibayashi, Kyoto (JP)

(73) Assignees: Panasonic Corporation, Osaka (JP); Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 12/766,571

(22) Filed: Apr. 23, 2010

Related U.S. Application Data

(60) Provisional application No. 61/172,887, filed on Apr. 27, 2009.

(51) Int. Cl.
*G01N 33/48* (2006.01)

(52) U.S. Cl. ............. 436/64; 436/63; 436/127; 436/129

(58) Field of Classification Search .................... 436/63, 436/64, 127, 129, 173
See application file for complete search history.

(56) References Cited

U.S. PATENT DOCUMENTS

| | | | |
|---|---|---|---|
| 2006/0160237 A1* | 7/2006 | Du | 436/129 |
| 2010/0126254 A1* | 5/2010 | Du | 73/61.52 |

* cited by examiner

*Primary Examiner* — Maureen M Wallenhorst
(74) *Attorney, Agent, or Firm* — McDermott Will & Emery LLP

(57) ABSTRACT

The present invention relates to a method for determining whether or not a mammal is affected with a lung cancer. The method for determining whether or not a mammal is affected with a lung cancer of the present invention includes the steps of:
 (a) measuring a concentration of 2-hydroxy-3-methylbutyric acid contained in the urine excreted from the mammal; and
 (b) determining that the mammal is affected with a lung cancer if the concentration measured in the step (a) is 13.2 μM or more.

1 Claim, 2 Drawing Sheets

METHOD FOR DETERMINING WHETHER OR NOT A MAMMAL IS AFFECTED WITH A LUNG CANCER

This application claims priority to provisional application Ser. No. 61/172,887, filed on Apr. 27, 2009.

BACKGROUND OF THE INVENTION

1. Field of the Invention

The present invention relates to a method for determining whether or not a mammal is affected with a lung cancer.

2. Description of the Related Art

Substances (a kind of proteins) that exist in a large amount only in cancer cells but either do not exist, or even though exist, do exist in just a slight amount in normal cells have been known. Such proteins are referred to as "tumor markers". Tumor marker tests, in general, quantitatively determine a tumor marker in blood, and have been used for the purpose of aiding diagnosis of cancer, or confirming the degree of progression of cancer.

Conventional tumor markers are high molecular substances such as hormones, enzymes, isozymes or fragmented proteins. Since there are great differences among individuals in blood levels of these conventional tumor markers, usability in diagnosing cancer has been unsatisfactory due to occurrence of false negative and false positive.

SUMMARY OF THE INVENTION

The present inventors investigated utilization of a low molecular compound, to which attention has not been drawn hitherto, as a tumor marker, and consequently discovered that by quantitatively determining 2-hydroxy-3-methylbutyric acid in urine excreted from a mammal, determination is enabled as to whether or not the mammal is affected with a lung cancer. Accordingly, the present invention was accomplished.

The present invention relates to a method for determining whether or not a mammal is affected with a lung cancer, the method comprising the steps of:

(a) measuring a concentration of 2-hydroxy-3-methylbutyric acid contained in the urine excreted from the mammal; and (b) determining that the mammal is affected with a lung cancer if the concentration measured in step (a) is 13 µM or more.

According to the present invention, a method of determination is provided which is useful for diagnosing lung cancer in mammals.

The above objects, other objects, features and advantages of the present invention will be apparent from the following detailed description of preferred embodiments with reference to attached drawings.

BRIEF DESCRIPTION OF THE DRAWINGS

FIG. 1 (b) shows an ion chromatogram of cancer-bearing mouse urine subjected to an ultrafiltration treatment.

FIG. 2 (b) shows an MS/MS spectrum of the specified component A shown in FIG. 2 (a).

FIG. 2 (c) shows an ion chromatogram of 2-hydroxy-3-methylbutyric acid.

FIG. 2 (d) shows an MS/MS spectrum of 2-hydroxy-3-methylbutyric acid.

DETAILED DESCRIPTION OF PREFERRED EMBODIMENTS

Figure 1A:
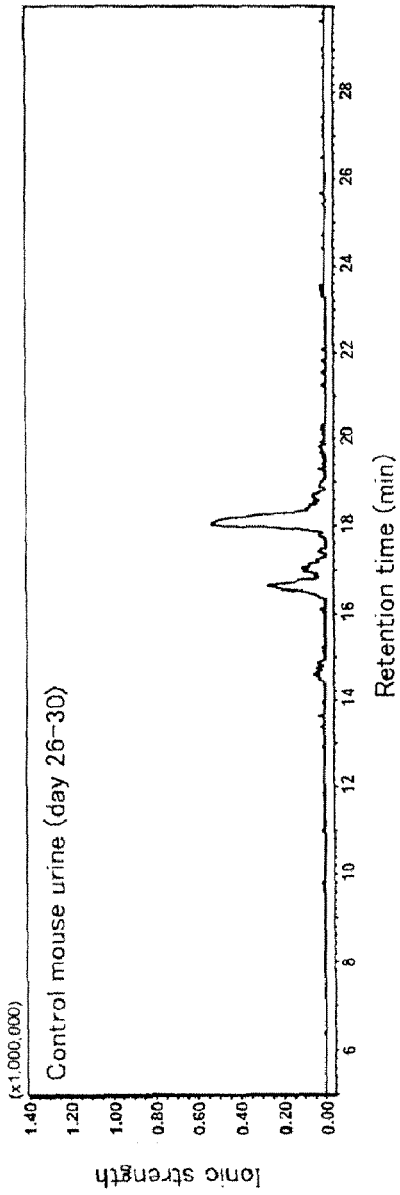
FIG. 1 (a) shows an ion chromatogram of control mouse (normal mouse) urine subjected to an ultrafiltration treatment.

1. Production Method of Cancer-bearing Mouse, and Urine Collection Method

1.1 Animals Used for Experiments

As immunocompromised mice, C.B-17/Icr-scid/scid Jcl (CLEA Japan, Inc.), 5 weeks-old male (50 animals) and female (15 animals) mice were used. The mice were fed separately in a glass metabolism cage for mouse (Metabolica, manufactured by Sugiyama-Gen Co., Ltd.). The mice were fed with CE-2 (CLEA Japan, Inc.) sterilized with radioactive ray as a chow, and given purified water which had been subjected to steam sterilization under pressure (121° C., 30 min) as drinking water.

1.2 Cells for Transplantation

A549 (DS Pharma Biomedical Co., Ltd.) that is a lung cancer cell line derived from human was used as cells for transplantation. Using a DMEM medium containing 10% fetal calf serum (FBS), A549 cells were proliferated by culturing at 37° C., in the presence of 5% $CO_2$.

1.3 Production of Cancer-Bearing Mouse

With respect to all individuals of the mice, the body weight was measured using an electronic balance (BJ600, manufactured by Sartorius K.K.). Then, the mice were grouped such that the average body weight of each group became equalized. The cancer-bearing group included 29 male mice and 17 female mice, whereas the control group (normal group) included 9 male mice and 5 female mice. A549 cells proliferated by culture were recovered, and transplanted into the mice of the cancer-bearing group subcutaneously at the right abdomen in an amount of $5 \times 10^7/0.1$ ml/mouse.

1.4 Urine Collection Method

Collection of the urine from mice was carried out on both the cancer-bearing group and the control group. The day on which A549 cells were transplanted into the mice of the cancer-bearing group was defined as test day 0, and the urine was collected every day until test day 30. The mouse was retained, and the urine collected into a 0.5 ml tube was provided as fresh urine. The fresh urine was stored at −80° C.

2. Pretreatment of Urine Sample

2.1 Thawing of Urine Sample

The fresh urine from the male mouse which had been freeze preserved at −80° C. (urine collected on day 26 to day 30 from starting the test) was thawed on ice. The fresh urine in a plurality of 0.5 ml tubes was assembled in a single 1.5 ml tube.

2.2 Ultrafiltration Treatment

The thawed fresh urine was subjected to centrifugal separation using Millipore Ultrafree-MC filters (UFC3 LGC 00, MW: 10,000, manufactured by Millipore) at 7,000 G at 0° C. for 90 min to allow for ultrafiltration of the fresh urine. The urine left on the filter was set on a new filter, and a similar operation was repeated. The urine that passed through the filter was set on a Microcon centrifugation system filter unit YM-3 (MW: 3,000, manufactured by Millipore), and an operation similar to that described above was carried out. The filtrate obtained by this operation was dispensed 50 µl each into 0.5 ml tubes, and stored at −80° C. until mass spectrometry was carried out.

Figure 1B:
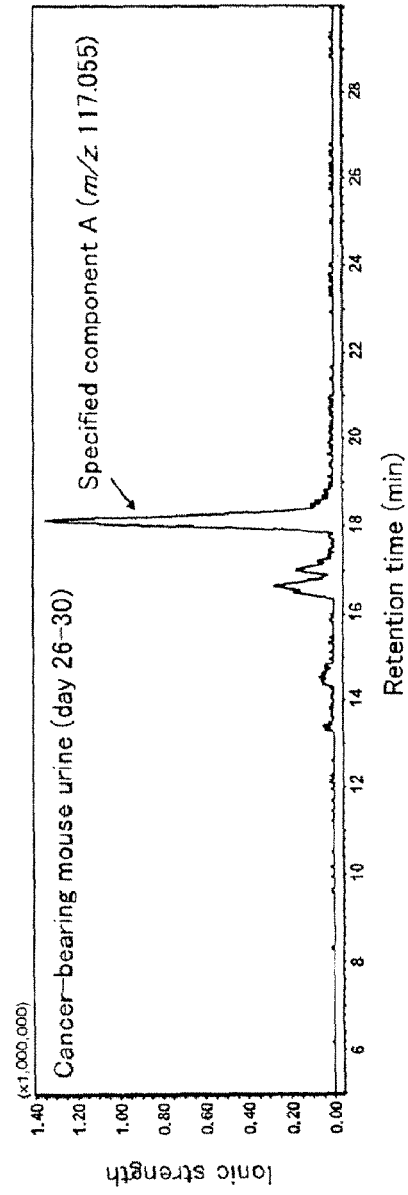
Figure 2:
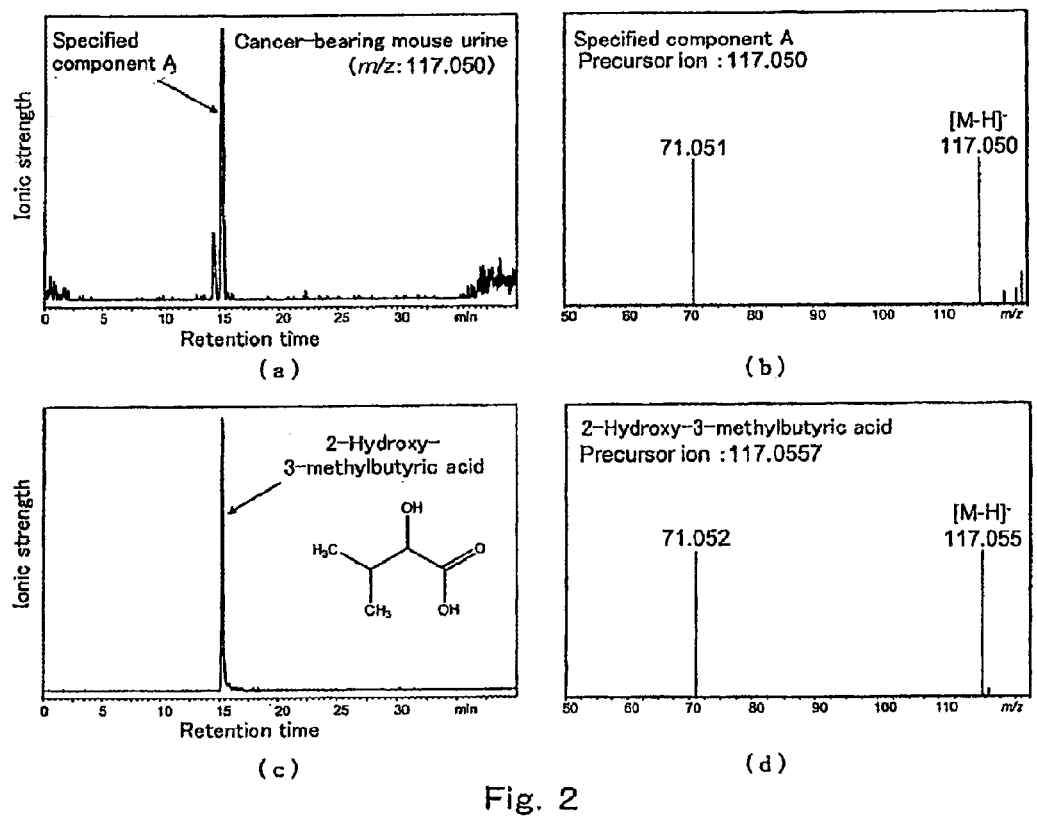
FIG. 2 (a) shows an extracted ion chromatogram of a specified component A in cancer-bearing mouse urine.

3. Mass Spectrometry
  3.1 Reagents and Apparatuses
  As reagents for use in the mass spectrometry, acetonitrile for HPLC (Wako Pure Chemical Industries, Ltd.) and formic acid for LC/MS (Wako Pure Chemical Industries, Ltd.) were used.
  Upon the mass spectrometry, a high performance liquid chromatograph (manufactured by Shimadzu Corporation, Prominence series) and a mass spectrometer (manufactured by Shimadzu Corporation, LCMS-IT-TOF) were used.
  3.2 Analysis Conditions
  Experimental conditions of the mass spectrometry were as in the following.
    Column: Develosil RPAQUEOUS-AR (internal diameter: 2.0 mm, length: 250 mm, particle size: 5 μm)
    Column temperature: 40° C.
    Flow rate: 0.2 ml/min
    Mobile phase: solvent A: 0.1% aqueous formic acid solution, and
    solvent B: 0.08% formic acid/acetonitrile
    Gradient condition:
      A:B=100:0 (0 min)→100:0 (5 min)→80:20 (45 min)→70:30 (55 min)→50:50 (70 min)→5:95 (71 min)→5:95 (75 min)
    Amount of infusion: 5 μl
    Ionization method: ESI+, ESI−
4. Identification and Quantitative Determination of Specified Component that Serves as A Cancer Marker
  4.1 Confirmation of Specified Component A
  A lung cancer cell culture fluid and a normal cell culture fluid were subjected to an ultrafiltration treatment in a similar manner to the fresh urine, and comparison of total ion chromatogram of the filtrate was made. A peak increased in the lung cancer cell culture fluid was confirmed by visual inspection, which was denoted as a specified component A. Comparison of the total ion chromatogram of the filtrate was made also with regard to the urine from the control mouse and the cancer-bearing mouse, and it was confirmed that the concentration of the specified component A increased in the cancer-bearing mouse urine (FIG. 1 (b)) than in the control mouse urine (FIG. 1 (a)). The m/z value of the specified component A was 117.055 [M-H]− as in FIG. 1 (a) and FIG. 1 (b).
  4.2 Searching of Candidate Compound
  A compound to be the candidate for the specified component A was searched on a database. On the basis of the m/z value of the specified component A (117.055 [M-H]−) obtained by the mass spectrometry, a candidate compound was searched using a compound database Madison Metabolomics Consortium Database (http://mmcd.nmrfam.wisc.edu/). Furthermore, using MassBank.jp (http://www.massbank.jp/) which is an MS/MS spectral database, the MS/MS spectral pattern of the specified component A was confirmed as to whether or not it agrees with the MS/MS spectral pattern on the database. As a result, the m/z value of the specified component A obtained by the mass spectrometry, and the MS/MS spectral pattern agreed with the information of 2-hydroxy-3-methylbutyric acid (m/z: 117.055 [M-H]− (measured)) retrieved from the database.
  4.3 Preparation of Standard Sample and Identification of Specified Component A
  For the purpose of identifying the specified component A, 2-hydroxy-3-methylbutyric acid (Sigma-Aldrich Corporation) was purchased, and using a 2-hydroxy-3-methylbutyric acid solution as a standard solution, an LC-MS/MS analysis was carried out. The 2-hydroxy-3-methylbutyric acid was dissolved in 50% DMSO aqueous solution, which was provided as a primary standard solution. Furthermore, the primary standard solution was diluted in water to produce a 10 μM standard solution for analysis. With respect to this standard solution for analysis, the LC-MS/MS analysis was carried out. As a result, the retention time and the MS/MS spectral data of the specified component A (FIG. 2 (a) and FIG. 2 (b)) were confirmed to agree with the retention time and the MS/MS spectral data of 2-hydroxy-3-methylbutyric acid in the standard solution for analysis (FIG. 2 (c) and FIG. 2 (d)). Thus, the specified component A was identified to be 2-hydroxy-3-methylbutyric acid.
  4.4 Production of Calibration Curve
  For the purpose of measuring the concentration of 2-hydroxy-3-methylbutyric acid in the cancer-bearing mouse urine, standard solutions for producing a calibration curve were prepared by diluting the primary standard solution in water to give the concentrations of 10 μM, 5 μM, 2 μM and 1 μM. A calibration curve was produced by plotting the concentrations and the peak areas of these standard solutions for producing a calibration curve. The concentration of 2-hydroxy-3-methylbutyric acid in the urine of the cancer-bearing mouse and the control mouse was calculated on the calibration curve. As a result, the concentration of 2-hydroxy-3-methylbutyric acid in the urine was 13.2 μM in the cancer-bearing mouse, and 11.7 μM in the control mouse, as shown in Table 1.

TABLE 1

Peak Area in Urine and Concentration in Urine of 2-hydroxy-3-methylbutyric acid

|  | Cancer-bearing mouse (day 26-30) | Control mouse (day 26-30) |
| --- | --- | --- |
| First analysis peak area | 11351776 | 9026914 |
| Second analysis peak area | 10162931 | 9151234 |
| Third analysis peak area | 10123641 | 9743683 |
| Mean peak area | 10546116 | 9307277 |
| Concentration in urine (μM) | 13.2 | 11.7 |

From the aforementioned experimental results, it was confirmed that 2-hydroxy-3-methylbutyric acid is detected at a concentration of 13.2 μM or more in urine excreted from a mammal affected by lung cancer. For almost all conventional tumor markers, it has been necessary to collect blood from a patient, and then measure the concentration of the tumor marker in plasma. However, according to the present invention, since the tumor marker which is a target of detection is a component in urine, an inspection sample can be noninvasively obtained without imposing a burden to the patient. According to the present invention, an efficient determination as to whether or not a mammal is affected with a lung cancer is enabled.

What is claimed is:
1. A method for determining whether or not a mammal is affected with a lung cancer, said method comprising the steps of:
  (a) measuring a concentration of 2-hydroxy-3-methylbutyric acid contained in the urine excreted from the mammal; and
  (b) determining that the mammal is affected with a lung cancer if the concentration measured in the step (a) is 13.2 μM or more.

* * * * *

UNITED STATES PATENT AND TRADEMARK OFFICE
CERTIFICATE OF CORRECTION

PATENT NO. : 8,008,084 B1
APPLICATION NO. : 12/766571
DATED : August 30, 2011
INVENTOR(S) : Yosuke Hanai et al.

It is certified that error appears in the above-identified patent and that said Letters Patent is hereby corrected as shown below:

On the Title Page, Item (73) Assignee presently reads Panasonic Corporation and Monell Chemical Senses Center and the correct Assignee should read PANASONIC CORPORATION.

Signed and Sealed this
Fourth Day of October, 2011

David J. Kappos
*Director of the United States Patent and Trademark Office*